United States Patent
Ichihara et al.

(10) Patent No.: US 8,334,394 B2
(45) Date of Patent: Dec. 18, 2012

(54) SOLID PHASE REACTION SYSTEM FOR OXIDATION

(75) Inventors: Jyunko Ichihara, Suita (JP); Syunrou Yamaguchi, Suita (JP)

(73) Assignee: Osaka University, Osaka (JP)

( * ) Notice: Subject to any disclaimer, the term of this patent is extended or adjusted under 35 U.S.C. 154(b) by 615 days.

(21) Appl. No.: 12/524,667

(22) PCT Filed: Jan. 30, 2008

(86) PCT No.: PCT/JP2008/051376
§ 371 (c)(1),
(2), (4) Date: Jul. 27, 2009

(87) PCT Pub. No.: WO2008/093711
PCT Pub. Date: Aug. 7, 2008

(65) Prior Publication Data
US 2010/0113807 A1  May 6, 2010

(30) Foreign Application Priority Data
Jan. 31, 2007 (JP) ................................. 2007-022073

(51) Int. Cl.
*C07D 303/00* (2006.01)
*C07D 301/02* (2006.01)

(52) U.S. Cl. .......................... 549/518; 549/512; 549/513
(58) Field of Classification Search .................. 549/512, 549/513, 518
See application file for complete search history.

(56) References Cited

FOREIGN PATENT DOCUMENTS

| | | | |
|---|---|---|---|
| JP | 62-234550 A | | 10/1987 |
| JP | 5-237392 A | | 9/1993 |
| JP | 8-27136 A | | 1/1996 |
| JP | 11-80144 A | | 3/1999 |
| JP | 2000-159693 A | | 6/2000 |
| JP | 2001-17863 A | | 1/2001 |
| JP | 2001-213871 A | | 8/2001 |
| JP | 2002-59007 A | | 2/2002 |
| JP | 2002-69079 A | | 3/2002 |
| JP | 2005-104902 | * | 4/2005 |
| JP | 2005-104902 A | | 4/2005 |

OTHER PUBLICATIONS

97th CATSJ Meeting, Abstracts: No. 2B 04, vol. 48, No. 2 (2006).

* cited by examiner

*Primary Examiner* — Taylor Victor Oh
(74) *Attorney, Agent, or Firm* — Birch, Stewart, Kolash & Birch, LLP

(57) ABSTRACT

A solid phase reaction system for oxidation of an organic compound,
having high industrial value in which an organic solvent exerting a reverse influence on earth environments is not necessary, reuse of a catalyst is possible, and high yield can be attained,
comprising
  a mixture of a powdery dispersion medium and a powder of a solid catalyst for the above-described oxidation reaction, and the above-described organic compound and aqueous hydrogen peroxide,
  wherein the above-described organic compound, the above-described solid catalyst and the above-described aqueous hydrogen peroxide are dispersed in the above-described mixture so that they get into contact mutually.

7 Claims, No Drawings

SOLID PHASE REACTION SYSTEM FOR OXIDATION

TECHNICAL FIELD

The present invention relates to a reaction system for oxidizing an organic compound with aqueous hydrogen peroxide. More particularly, the present invention relates to a solid phase reaction system for oxidation of an organic compound with aqueous hydrogen peroxide, in a solid phase system using a powdery dispersion medium.

BACKGROUND ART

As the oxidation reaction of an organic compound applied to production of an epoxy compound by oxidation of olefins, production of aldehydes and ketones by oxidation of alcohols, and the like, there is known a reaction using hydrogen peroxide as an oxidizing agent and carried out in a two phase heterogeneous system composed of an organic phase containing a dissolved organic compound as an oxidation subject, and of a aqueous hydrogen peroxide solution. Further, there is also suggested a specific catalyst for improving the conversion rate of olefins and the selectivity of an epoxy compound in this reaction.

For example, patent document 1 discloses a method of carrying out epoxidation by reacting olefins and aqueous hydrogen peroxide with a halogenated hydrocarbon as a solvent, using a catalyst such as polyacids and the like. This method, however, has a problem of use of a halogenated hydrocarbon harmful for earth environments. As a method using no halogenated hydrocarbon, patent document 2 discloses a method of oxidizing olefins with aqueous hydrogen peroxide, in the presence of α-aminomethylphosphonic acid, tungstic acids and phase transfer catalyst, in a non-halogenated organic solvent such as aromatic hydrocarbons and the like.

However, these methods have problems that when hydrogen peroxide of high concentration is used, an intensive reaction accompanied by heat generation tends to occur, there is a necessity of use of aqueous hydrogen peroxide of low concentration for safety, and recovery of a catalyst after the reaction and treatment of waste water after the reaction become difficult, and the like. Further, in these methods, the yield of the product (selectivity×conversion rate) is also unsatisfactory. That is, the oxidation reaction of an organic compound carried out in a two phase heterogeneous system composed of an organic phase and a hydrogen peroxide aqueous solution has problems from the standpoint of earth environments and from the industrial standpoint.

As a method for solving this problem, patent document 3 discloses a method of oxidizing olefins using a urea-hydrogen peroxide powder as an oxidizing agent, in a powdery dispersion medium composed of hydrotalcites, using polyacids or specific metal oxides as a catalyst. This method is carried out in a solid phase, and has merits that an organic solvent exerting a reverse influence on earth environments is not required, the conversion rate and selectivity are high, reuse of a catalyst is possible, and the like.
(Patent document 1) JP-A No. 62-234550
(Patent document 2) JP-A No. 8-27136
(Patent document 3) JP-A No. 2005-104902

SUMMARY OF THE INVENTION

Problems to be Solved by the Invention

The urea-hydrogen peroxide powder used as an oxidizing agent in this method has a merit that handling thereof in the reaction is easy. However, a problem of accumulation of urea after consumption of hydrogen peroxide by the reaction in the solid phase reaction system occurs. Then, operations for removal of urea, for example, washing with acetone, alcohol mixed aqueous solution and the like, drying with heating at 100° C. to 200° C., and the like, are necessary. However, as a result, the reaction operations are complicated, leading to decrease in a value as in industrial production method.

Thus, it is desired to develop a solid phase reaction system for oxidation having the merit described above and having merits of uncomplicated reaction operations such as no necessity of washing after the reaction, and the like, and having a higher industrial value. Further, it is also desired to improve the production efficiency by an increase of the reaction rate and an improvement in the yield of the product, and by rendering an operation of isolation of the product and an operation of recovery of a solid catalyst phase easy, and the like.

Considering such situations mentioned above, the present invention has an object of providing a solid phase reaction system for oxidation of an organic compound having merits that an organic solvent exerting a reverse influence on earth environments is not necessary, the conversion rate and selectivity are high (namely, the yield of the product is high), reuse of the catalyst is possible, and the like, and needing no process of complicating the reaction operation, showing high reaction rate, giving easiness in operations of isolation and recovery of the product, and providing a high industrial value.

Means for Solving the Problems

The present inventors have intensively studied to attain the above-described object and resultantly found that the above-described object can be attained by use of aqueous hydrogen peroxide instead of a urea-hydrogen peroxide powder in the above-described solid phase reaction system for oxidation described in patent document 3, and have completed the present invention.

Conventionally, when aqueous hydrogen peroxide is used for an oxidation reaction in a liquid phase, a catalyst cluster is decomposed, to generate several active species, and the production ratio of these active species varies [D. C. Duncan, R. C. Chambers, E. Hecht, C. L. Hill, J. Am. Chem. Soc. 117 (1995) 681]. Therefore, there is a problem of causing a decrease in the selectivity of the product and a decrease in the utilization efficiency of hydrogen peroxide, and an excellent oxidation reaction cannot be carried out. However, the present inventors have intensively studied and resultantly found that in a solid phase system, if the concentration of aqueous hydrogen peroxide is adjusted in a given range, this problem does not occur and additionally, and, while maintaining the above-described merit of the conventional solid phase reaction system for oxidation, the reaction rate and the yield of the product are also improved, and operations of isolation and recovery of the production also become easy.

The present inventors have also found that in a solid phase reaction system for oxidation, even aqueous hydrogen peroxide of high concentration can be used safely, and the practical yield of the product is also obtained.

The present inventors have further found that in the above-described solid phase reaction system for oxidation described in patent document 3, if other specific powdery dispersion mediums are used instead of hydrotalcites, the reaction rate is improved remarkably, obtaining a solid phase reaction system for oxidation having a higher industrial value. The present inventions explained below have been completed based on these findings.

The first embodiment of the present invention is a solid phase reaction system for oxidation of an organic compound comprising a mixture of a powdery dispersion medium and a powder of a solid catalyst for the above-described oxidation reaction, the above-described organic compound, and aqueous hydrogen peroxide having a concentration of 5% or more and less than 35%, wherein the above-described organic compound, the above-described solid catalyst and the above-described aqueous hydrogen peroxide are dispersed in the above-described mixture so that they get into contact mutually.

The second embodiment of the present invention is a solid phase reaction system for oxidation of an organic compound comprising a mixture of a powdery dispersion medium and a powder of a solid catalyst for the above-described oxidation reaction, the above-described organic compound, and aqueous hydrogen peroxide having a concentration of 35% or more and 60% or less, wherein the above-described organic compound, the above-described solid catalyst and the above-described aqueous hydrogen peroxide are dispersed in the above-described mixture so that they get into contact mutually.

The third embodiment of the present invention is a solid phase reaction system for oxidation of an organic compound comprising a mixture of a powdery dispersion medium selected from the group consisting of apatite, diatomaceous earth and calcium fluoride and a powder of a solid catalyst for the above-described oxidation reaction, the above-described organic compound and aqueous hydrogen peroxide, wherein the above-described organic compound, the above-described solid catalyst and the above-described aqueous hydrogen peroxide are dispersed in the above-described mixture so that they get into contact mutually.

All of the above-described first, second and third embodiments of the present invention are characterized in that a mixture of a powdery dispersion medium and a powder of a solid catalyst is used, and aqueous hydrogen peroxide and organic compound are added to a powder of this mixture to allow them contact, to oxidize the organic compound. In the oxidation reaction in the above-described two phase heterogeneous system, a solvent is used and an oxidation reaction is carried out in a liquid phase. However, in the present invention, a powdery dispersion medium is used as a solid medium instead of a solvent, and for example, a solid catalyst is mixed into this powder of dispersion medium, and an organic compound and aqueous hydrogen peroxide as reaction reagents are added to the mixture, and an oxidation reaction is carried out while maintaining the apparent powdery state. Therefore, an organic solvent exerting a reverse influence on earth environments is not required. Further, it is characterized in that there is no need of mixing of the reaction system during the oxidation reaction, and the oxidation reaction can be carried out even under condition of still standing. As the method of mixing a powdery dispersion medium, solid catalyst, organic compound and aqueous hydrogen peroxide, there are mentioned, in addition to the method described above, a method in which an organic compound is added to a powdery dispersion medium containing a solid catalyst, and this powder is mixed with another powdery dispersion medium containing aqueous hydrogen peroxide, a method in which an organic compound and hydrogen peroxide are separately allowed to permeate into powdery dispersion mediums, then, the powdery dispersion mediums and a solid catalyst are mixed, and other methods. The method is not particularly restricted providing an oxidation reaction can be carried out while maintaining apparent powdery state.

Here, as the powdery dispersion mediums, used are powders having a nature which disperses a solid catalyst, aqueous hydrogen peroxide and organic compound, does not degrade by them, and does not disturb the oxidation reaction, preferably powders having a nature which promotes the oxidation reaction. As the powdery dispersion medium to be used in the above-described first and second embodiments, specifically exemplified are phosphates such as apatite and the like, clays such as diatomaceous earth [main component: silica], kaolin [main component: silica alumina], hydrotalcite and the like, fluorides such as calcium fluoride and the like, and oxides such as silica, titania, alumina and the like. Of them, powdery dispersion mediums selected from phosphates, diatomaceous earth, silica, alumina, kaolin, silica alumina and calcium fluoride are preferable, and capable of attaining higher yield. Particularly, in the case of the above-described third embodiment, using a powdery dispersion medium selected from apatite, diatomaceous earth and calcium fluoride, further higher yield can be obtained.

Here, the apatite is a kind of calcium phosphate, and fluorapatite, chlorapatite, carbonate apatite, hydroxyapatite and the like are present as apatite-type minerals. Of them, fluorapatite is more preferably used.

Diatomaceous earth is a soft rock or soil composed mainly of a husk of Bacillariophyta, and silica is a main component, although alumina, iron oxide, alkali metal oxides and the like are often contained in addition to silica. Those which are porous, having high void ratio and having a cake bulk density of about 0.2 to 0.45 are used in many cases. Among diatomaceous earths, calcined products are preferable, or freshwater diatomaceous earths are preferable, and it is also possible to use other diatomaceous earths. As specific examples of such diatomaceous earths, those marketed under the trade name of Celite (registered trademark) from Celite Co. and those marketed under the trade name of Celatom from Eagle Picher Minerals are exemplified. Further, those calcined together with sodium carbonate and the like can also be used.

Hydrotalcites are composed of at least one selected from the group consisting of $(M^{2+})_{1-x}(M^{3+})_x(OH)_2(A^{n-})_{x/n}\cdot aH_2O$ (wherein, $M^{2+}$ represents a divalent metal ion, $M^{3+}$ represents a trivalent metal ion, $A^{n-}$ represents an n valent anion, and x and a represent ranges of $0<x<0.5$ and $0\leq a<1$, respectively). $M^{2+}$ includes Mg, Ca or Zn, $M^{3+}$ includes Al or Fe, $A^{n-}$ includes $OH^-$, $ClO_4^-$, $NO_3^-SO_4^{2-}$, $CO_3^{2-}$, $SiO_3^{2-}$, $HPO_4^{2-}$, $PO_4^{3-}$ or $CH_3COO^-$.

As the solid catalyst, exemplified are oxides of metals selected from the group consisting of tungsten, molybdenum and vanadium, oxyacids containing metals selected from the group consisting of tungsten, molybdenum and vanadium and salts thereof, and oxides, halides and sulfates of elements selected from the group consisting of iron, manganese and ruthenium.

The oxides of metals selected from the group consisting of tungsten, molybdenum and vanadium include $WO_3$, $MoO_3$ and $V_2O_5$. The oxyacids containing metals selected from the group consisting of tungsten, molybdenum and vanadium and salts thereof include tungstates such as tungstic acid $(H_2WO_4)$, $Na_2WO_4$ and the like, molybdates such as molybdic acid $(H_2MoO_4)$, $Na_2MoO_4$ and the like, vanadates such as vanadic acid, $NH_4VO_3$ and the like, isopolyacids containing tungsten, molybdenum or vanadium and salts thereof, heteropolyacids containing tungsten, molybdenum or vanadium and salts thereof. The above-described isopolyacids and heteropolyacids containing tungsten, molybdenum or vanadium include also composites represented by $Q_3[PW_6Mo_6O_{40}]$, $Q_7[PV_4Mo_8O_{40}]$ and the like, and peroxo type compounds represented by $Q_3\{PO_4[W(O)(O_2)]_4\}$, $Q_2[W_2O_3(O_2)_4]$ and the like. (In the formulae, Q represents a counter cation).

The hetero atoms in the above-described heteropolyacids include phosphorus, boron, silicon, germanium, lanthanoid elements, manganese, nickel, iron, cobalt or ruthenium and the like. The counter cations of the above-described salts of isopolyacids or salts of heteropolyacids include organic cations such as tetrabutylammonium, butylammonium, benzyltrimethylammonium, cetylpyridinium and the like, and inorganic cations such as ammonium, potassium, sodium, calcium and the like.

More specifically, the isopolytungstates containing tungsten include $(NH_4)_6W_7O_{24}$, $(NH_4)_{10}[H_2W_{12}O_{42}]$, $(CetylPy)_{10}[H_2W_{12}O_{42}]$, $(CetylPy)_4[W_{10}O_{32}]$, $K_4[W_{10}O_{32}]$ and the like, and the heteropolytungstates containing tungsten include $(CetylPy)_3[PW_{12}O_{40}]$, $(CetylPy)_5H_2[PW_{11}O_{39}]$, $Na_9[PW_9O_{34}]$ and the like, and further exemplified are those obtained by substituted phosphorus (P) in the above-described heteropolytungstates by boron (B), silicon (Si), germanium (Ge) and the like. CetylPy in the formulae represents cetylpyridinium.

As the oxyacids containing molybdenum and salts thereof, exemplified are compounds obtained by substitution of tungsten, by molybdenum, in the compounds exemplified as the above-described oxyacids containing tungsten and salts thereof. As the oxyacids containing vanadium and salts thereof, exemplified are compounds obtained by substitution of tungsten, by vanadium, in the compounds exemplified as the above-described oxyacids containing tungsten and salts thereof.

Among the above-described solid catalyst, catalysts selected from the group consisting of the oxides of tungsten or molybdenum, the isopolyacids containing tungsten or molybdenum and the heteropolyacids containing tungsten or molybdenum are preferably exemplified. Particularly, catalysts selected from the group consisting of the isopolyacids or heteropolyacids containing tungsten are preferable since higher selectivity is obtained with them.

The oxides, halides and sulfates of elements selected from the group consisting of iron, manganese and ruthenium include $FeCl_3$, $MnSO_4$, $RuCl3$ and the like.

The solid catalyst is not required to be immobilized to a powdery dispersion medium, and it may be permissible to simply mix a powder of a solid catalyst and a powder of a powdery dispersion medium. For example, a mixture as a solid phase in the oxidation reaction system of the present invention can be obtained by a method in which a powder of a solid catalyst is added previously to a dried powdery dispersion medium, and the powders are mixed with stirring. The particle sizes of the powder of a solid catalyst and the powdery dispersion medium are not particularly restricted, and powders having a particle size of about 5 to 100 μm which are available easily can be used, and the effects of the present invention such as higher yield of the product and the like can be obtained.

The solid phase reaction system for oxidation of the present invention is formed by adding aqueous hydrogen peroxide and an organic compound (substrate) as the oxidation subject into a mixture of a powdery dispersion medium and a powder of a solid catalyst obtained as described above. This addition is so carried out that both of them are dispersed in the above-described mixture and get into mutual contact. Mixing with stirring may also be performed after the addition to render dispersion and mutual contact of both components excellent. However, after this, the reaction may be carried out under condition of still standing of this mixture, and there is no need to carry out mixing and stirring.

The amount of an organic compound and aqueous hydrogen peroxide is an amount with which the oxidation reaction system keeps the apparent powdery state. When the concentration of aqueous hydrogen peroxide is about 30%, the powdery dispersion medium and solid catalyst can be used in an amount in the range of about 0.1 to 5 g, preferably 0.5 to 3.0 g, with respect to 1 mM of the organic compound (substrate). However, since the capacity of aqueous hydrogen peroxide varies depending on the concentration of the aqueous hydrogen peroxide, the favorable amount range of the powdery dispersion medium and solid catalyst also changes according to this variation.

When the powdery dispersion medium and solid catalyst are used in an amount in the range of about 0.5 to 1.0 g, with respect to 1 mM of the organic compound (substrate), the organic compound and aqueous hydrogen peroxide are present in the form of a phase having a thickness of about 10 to 20 nm on the surface of dispersion particles (particles of powdery dispersion medium and solid catalyst) having a particle size of about 5 to 40 μm. It is believed that the reaction continues by movement of the organic compound and aqueous hydrogen peroxide thus present on the surface of dispersion particles, on the surface of the particle under a suitable mutual action. The reaction under such a powdery state progresses under an environment different utterly from that for a bulk liquid phase system, even if the same reaction reagent is used.

The first embodiment of the present invention is characterized in that aqueous hydrogen peroxide having a concentration of 5% or more and less than 35% is used. In the case of use of aqueous hydrogen peroxide of low concentration in the conventional oxidation reaction to be carried out in a two phase heterogeneous system composed of an organic phase and aqueous hydrogen peroxide, the produced epoxide is hydrolyzed to generate by-products such as diols and the like to lower the selectivity of the intended product, while in the oxidation reaction system of the present invention, even in the case of use of aqueous hydrogen peroxide of low concentration, the selectivity is high, and the high yield of the intended product is obtained.

Further, the reaction rate is higher as compared also with a reaction system using as an oxidizing agent a urea-hydrogen peroxide powder in a solid phase system, and the high yield of the intended product which is not obtained in the case of use of a urea-hydrogen peroxide powder is obtained. Furthermore, in the case of use as an oxidizing agent of a urea-hydrogen peroxide powder in a solid phase system, there are problems such as need of washing and calcination after the reaction, and the like. However, the present invention does not include such problems, and, thereby, is an oxidation reaction system of high industrial use value.

The second embodiment of the present invention is characterized in that aqueous hydrogen peroxide having a concentration of 35% or more and 60% or less is used Aqueous hydrogen peroxide having a concentration of 35% or more and 60% or less has a high danger of handling so that transportation thereof is regulated, and in the reaction system in a two phase heterogeneous system, a sufficient reaction equipment is required for avoiding rapid heat generation and explosion. However, the present inventors have found that the reaction can be carried out more safely and the practical yield of the product is obtained, by the method of adding aqueous hydrogen peroxide into a solid phase, leading to completion of the invention according to this second embodiment.

The third embodiment of the present invention is characterized in that a powder selected from apatite, diatomaceous earth and calcium fluoride is used as a powdery dispersion medium. The present inventors have found that particularly higher yield is obtained if apatite, celite (diatomaceous earth) or calcium fluoride is used as a powdery dispersion medium in the above-described solid phase reaction system for oxidation, leading to completion of the invention according to this third embodiment.

All of the above-described first, second and third embodiments of the present invention can be applied to an epoxidation reaction of synthesizing an epoxy compound by oxidizing an organic compound having a carbon-carbon double bond. That is, the present invention provides the above-described solid phase reaction system for oxidation in which the above-described organic compound has a carbon-carbon double bond and the above-described oxidation is a reaction of inserting oxygen into the carbon-carbon double bond. As the organic compound having a carbon-carbon double bond, alkenes, cycloalkenes, allyl alcohols and the like can be mentioned.

All of the above-described first, second and third embodiments of the present invention can be applied to general oxidation reactions of an organic compound, such as an oxidation reaction of alcohol and sulfide, production of an N-oxide by oxidation of an organic compound having tertiary nitrogen, and the like, in addition to the epoxidation reaction.

That is, the present invention provides the above-described solid phase reaction system for oxidation in which the above-described organic compound is selected from organic compounds having a hydroxyl group, and the above-described oxidation reaction is a reaction of producing an aldehyde, ketone or carboxylic acid. For example, this oxidation reaction system can be applied to reactions for generating an aldehyde or ketone by oxidizing alcohols.

The present invention provides the above-described solid phase reaction system for oxidation in which the above-described organic compound is an organic compound having a sulfur atom and the above-described oxidation reaction is a reaction of generating a sulfoxide or sulfone from a sulfide, a reaction of generating a sulfone from a sulfoxide, or a reaction of oxidizing a thiol to give a disulfide.

Further, the present invention provides the above-described solid phase reaction system for oxidation in which the above-described organic compound is an organic compound having tertiary nitrogen and the above-described oxidation reaction is a reaction of generating an N-oxide of an organic compound having tertiary nitrogen. Here, the organic compound having tertiary nitrogen includes also aromatic nitrogen compounds such as pyridine, picoline, quinoline and the like, together with tertiary amines.

Effect of the Invention

According to the solid phase reaction system for oxidation of the present invention, oxidation of an organic compound can be carried out with high yield, and additionally, there are merits that an organic solvent exerting a reverse influence on earth environments is not necessary, reuse of a catalyst is possible, and the like. Further, a solid catalyst and a powdery dispersion medium constituting the solid phase can be reused only by performing a drying treatment after separation of the product, and a process of rendering the reaction operations complicated is not needed in reuse, and operations of isolation and recovery of the product are easy. Thus, owing to such features, the present invention is an organic compound solid phase reaction system for oxidation of high industrial value.

The solid phase reaction system for oxidation according to the first embodiment of the present invention performs the above-described excellent effect, and has an effect that the conversion rate and selectivity are high (therefore, the yield of the product is high). By the solid phase reaction system for oxidation according to the second embodiment of the present invention, also aqueous hydrogen peroxide of high concentration which cannot be used easily in the conventional two phase heterogeneous oxidation reaction system can be used safely, and practical yield can be obtained. By the solid phase reaction system for oxidation according to the third embodiment of the present invention, a remarkable effect of particularly high conversion rate and selectivity is obtained.

BEST MODES OF THE INVENTION

The best modes for carrying out the present invention will be illustrated based on examples shown below. The present invention is not limited to the following modes and examples. It is possible to apply various variations within the range which is the same as and equivalent to the present invention.

Example 1

Epoxidation Reaction of Cyclooctene

In a screwed test tube, 1.00 g of fluorapatite (FAp), a powdery dispersion medium, and 0.01 mmol of a solid catalyst (CetylPy)$_3$[PW$_{12}$O$_{40}$] were weighed, and 0.110 g (1.00 mmol) of cyclooctene was added to a mixture of them (hereinafter, referred to as solid mixed phase), and, then, the solid mixed phase was stirred well. Further, 0.10 mL (0.90 mmol) of 31% aqueous hydrogen peroxide was added thereto. Then, the solid mixed phase was stirred well, and thereafter, allowed to stand still at 25° C. The reaction tracking was performed by sampling small amount of the mixed phase every constant time, and using capillary gas chromatograph. After standing still at 25° C. for 24 hours, the reaction mixture in the solid mixed phase was extracted with pentane (5 mL×three times), and the solvent was evaporated from the extraction solution, to obtain 0.105 g of a colorless solid of epoxycyclooctane. The yield of the product (epoxide yield) was 86% (96% based on aqueous hydrogen peroxide). The results are shown in Table 1 and Table 3.

Comparative Example 1

Epoxidation Reaction of Cyclooctene in a Two Phase Heterogeneous System of Substrate/Aqueous Hydrogen Peroxide In a screwed test tube, 0.110 g (1.00 mmol) of cyclooctene, 0.10 mL (0.90 mmol) of 31% (by weight) aqueous hydrogen peroxide were added, and, further, 0.01 mmol of a solid catalyst (CetylPy)$_3$[PW$_{12}$O$_{40}$] was added. Then, while stirring well, the reaction was conducted at 25° C. for 24 hours. The yield of epoxycyclooctane is shown in Table 3.

Example 2

Epoxidation Reaction of Cyclooctene

The solid mixed phase after extraction in Example 1 was dried under reduced pressure for about 12 hours. 0.110 g (1.00 mmol) of cyclooctene was added to the solid mixed phase after drying under reduced pressure, and stirred well. Further, 0.10 mL (0.90 mmol) of 31% aqueous hydrogen peroxide was added and stirred well. Then, the mixture was allowed to stand still at 25° C. for 24 hours. Thereafter, a colorless solid of epoxycyclooctane was obtained in the same manner as in Example 1. The epoxide yield was 83%.

As show in the experiment results, according to the solid phase reaction system for oxidation of the present invention, the solid mixed phase can be reused only by drying without carrying out washing with alcohol or the like, calcination and the like. The decrease in yield by the reuse is also small.

Examples 3 to 9

The yields of epoxycyclooctanes produced in the same manner as in Example 1 excepting that the catalyst was changed to those shown in Table 1 are shown. The results thereof (epoxide yield after 24 hours) are shown in Table 1. All of the selectivities are 99% or more.

TABLE 1

| Example No. | Catalyst | Powdery dispersion medium | Epoxide yield After 7 hours | Epoxide yield After 24 hours |
|---|---|---|---|---|
| 1 | $(CetylPy)_3[PW_{12}O_{40}]$ | FAp | 42 | 86 |
| 3 | $(CetylPy)_{10}[H_2W_{12}O_{42}]$ | FAp | 92 | |
| 4 | $(NH_4)_3[PW_{12}O_{40}]$ | FAp | 16 | 69 |
| 5 | $WO_3$ | FAp | 9 | 36 |
| 6 | $H_2WO_4$ | FAp | 51 | 58 |
| 7 | $MoO_3$ | FAp | 13 | 44 |
| 8 | $(CetylPy)_3[PMo_{12}O_{40}]$ | FAp | 39 | 62 |
| 9 | $(NH_4)_3[PMo_{12}O_{40}]$ | FAp | 42 | 60 |

According to the experimental results, it is shown that excellent yields are obtained by any of the catalysts in the Table, and particularly, when isopolyacids or heteropolyacids of tungsten is used as the catalyst, the yields are high.

Example 10

Epoxidation Reaction of Cyclooctene (Example of Using 15% Aqueous Hydrogen Peroxide)

In a screwed test tube, 1.00 g of fluorapatite (FAp), a powdery dispersion medium, and 0.01 mmol of a solid catalyst $(CetylPy)_3[PW_{12}O_{40}]$ were weighed, and 0.110 g (1.00 mmol) of cyclooctene was added to the solid mixture of them, and, then, the solid mixed phase was stirred well. Further, 0.40 mL (1.76 mmol) of 15% aqueous hydrogen peroxide was added thereto. Then, the solid mixed phase was stirred well, and thereafter, allowed to stand still at 25° C. The epoxide yield after standing still at 25° C. for 24 hours was 96% (selectivity was 99% or more). According to the experimental results, it is shown that high yield and selectivity are obtained even when the concentration of aqueous hydrogen peroxide is low as 15%.

Example 11

Epoxidation Reaction of Cyclooctene (Example of Using 60% Aqueous Hydrogen Peroxide)

In a screwed test tube, 1.00 g of fluorapatite (FAp), a powdery dispersion medium, and 0.01 mmol of a solid catalyst $(CetylPy)_3[PW_{12}O_{40}]$ were weighed, and 0.110 g (1.00 mmol) of cyclooctene was added to the solid mixture of them, and, then, the solid mixed phase was stirred well. Further, 0.10 mL (1.76 mmol) of 60% aqueous hydrogen peroxide was added thereto. Then, the solid mixed phase was stirred well, and thereafter, allowed to stand still at 25° C. The epoxide yield after standing still at 25° C. for 24 hours was 76% (selectivity was 99% or more). According to the experimental results, it is shown that high selectivity and practical yield are obtained even when the concentration of aqueous hydrogen peroxide is high as 60%.

Example 12

Epoxidation Reaction of Cyclooctene 1.00 g of fluorapatite (FAp) and 0.01 mmol of a solid catalyst $(CetylPy)_3[PW_{12}O_{40}]$ were weighed, and 0.110 g (1.00 mmol) of cyclooctene and 0.11 mL (1.0 mmol) of 31% aqueous hydrogen peroxide were added to a mixture of FAp and $(CetylPy)_3[PW_{12}O_{40}]$ (hereinafter, referred to as solid mixed phase), and, then, the solid mixed phase was stirred well. Thereafter, the reaction was conducted according to the same manner as in Example 1. The epoxide yields after reacting 24 hours are shown in Table 2. The selectivity was 99% or more.

Examples 13 to 20

Epoxidation Reaction of Cyclooctene

The epoxide yields (after reacting 24 hours) of epoxycyclooctanes produced in the same manner as in Example 12 excepting that the powdery dispersion medium was changed to those shown in Table 2 are shown in Table 2. All of the selectivities are 99% or more.

TABLE 2

| Example No. | Powdery dispersion medium | Epoxide yield |
|---|---|---|
| 12 | FAp | 94 |
| 13 | diatomaceous earth* | 92 |
| 14 | diatomaceous earth** | 93 |
| 15 | $TiO_2$ | 42 |
| 16 | $CaF_2$ | 86 |
| 17 | hydrotalcite | 43 |
| 18 | kaolin | 79 |
| 19 | $Al_2O_3$ | 78 |
| 20 | $SiO_2$ | 70 |

*Celite521 (trade name, manufactured by Celite Corporation, pH 7.0)
**Celite545 (trade name, manufactured by Celite Corporation, pH 10.0)
FAp (manufactured by Taihei Chemical Industrial Co., Ltd.)
$TiO_2$ (manufactured by Wako Pure Chemical Industries, Ltd)
$CaF_2$ (manufactured by Morita Chemical Industries Co., Ltd)
$Al_2O_3$ and $SiO_2$ (Aldrich Reagent)

According to the experimental results, it is shown that excellent yields are obtained by any of the powdery dispersion mediums in the Table, and particularly, when fluorapatite, diatomaceous earth or calcium fluoride is used as the powdery dispersion medium, the yields are high.

Comparative Example 2

Epoxidation Reaction of Cyclooctene (in a Solid Phase Using a Urea-Hydrogen Peroxide Powder as an Oxidizing Agent)

In a screwed test tube, 1.00 g of fluorapatite (FAp), a powdery dispersion medium, 0.01 mmol of a solid catalyst $(CetylPy)_3[PW_{12}O_{40}]$, and a urea-hydrogen peroxide powder containing 1.00 mmol of hydrogen peroxide were weighed, and 0.110 g (1.00 mmol) of cyclooctene was added to the mixture of them. Then, the mixture was stirred well, and thereafter, allowed to stand still at 25° C. The yield of epoxycyclooctane is shown in Table 3.

Comparative Example 3

Epoxidation Reaction of Cyclooctene (in a Solid Phase Using a Urea-Hydrogen Peroxide Powder as an Oxidizing Agent)

In a screwed test tube, 1.00 g of hydrotalcite, a powdery dispersion medium, 0.01 mmol of a solid catalyst (CetylPy)$_3$[PW$_{12}$O$_{40}$], and a urea-hydrogen peroxide powder containing 1.00 mmol of hydrogen peroxide were weighed, and 0.110 g (1.00 mmol) of cyclooctene was added to the mixture of them. Then, the mixture was stirred well, and thereafter, allowed to stand still at 25° C. The yield of epoxycyclooctane is shown in Table 3.

TABLE 3

| No. | Powdery dispersion medium | Oxidizing agent | Reaction condition | Epoxide yield(%) |
|---|---|---|---|---|
| Example 1 | Solid state (FAp) | 31% aqueous hydrogen peroxide | 25° C. Stand still 24 hours | 86 |
| Comparative Example 1 | none | 31% aqueous hydrogen peroxide | 25° C. Stirring 24 hours | 56 |
| Comparative Example 2 | Solid state (FAp) | urea-hydrogen peroxide (Solid) | 25° C. Stand still 24 hours | 30 |
| Comparative Example 3 | Solid state (hydrotalcite) | urea-hydrogen peroxide (Solid) | 25° C. Stand still 24 hours | 38 |

According to the oxidation reaction system of the present invention (Example 1, a powdery dispersion medium/solid catalyst/aqueous hydrogen peroxide), a more excellent yield is obtained by far than no-solvent epoxidation reactions using a powdery dispersion medium/solid catalyst/solid hydrogen peroxide, conducted in Comparative examples 2 and 3, and epoxidation reactions in a two phase heterogeneous system of substrate/solid catalyst/aqueous hydrogen peroxide conducted in Comparative example 1. An excellent industrial value of the oxidation reaction system of the present invention is manifested.

Example 21

Epoxidation Reaction of 1-decene

In a screwed test tube, 1.00 g of fluorapatite (FAp) and 0.061 g (0.010 mmol) of a catalyst (CetylPy)$_{10}$[H$_2$W$_{12}$O$_{42}$] were weighed, and 0.144 g (1.02 mmol) of 1-decene was added to a solid mixture composed of them, and the mixture was stirred well. Further, 0.22 mL (2.0 mmol) of 31% aqueous hydrogen peroxide was added and the mixture was stirred well, then, allowed to stand still at 25° C. After 24 hours at 25° C., the correspondent epoxide was produced with a yield of 68% (selectivity 93%). Subsequently, the reaction was carried out at 25° C., and 70 hours after initiation of standing still at 25° C., extraction with a solvent was carried out in the same manner as in Example 1, and the solvent was evaporated, to obtain 0.143 g (yield 91%, selectivity 91%) of the correspondent epoxide.

Example 22

Epoxidation Reaction of 2-octene-1-ol

In a screwed test tube, 1.00 g of fluorapatite (FAp) and 0.061 g (0.010 mmol) of a catalyst (CetylPy)$_{10}$[H$_2$W$_{12}$O$_{42}$] were weighed, and 0.128 g (1.00 mmol) 2-octene-1-ol was added to a solid mixture composed of them, and the mixture was stirred well. Further, 0.11 mL (1.0 mmol) of 31% aqueous hydrogen peroxide was added and the mixture was stirred well then, allowed to stand still at 25° C. After 24 hours at 25° C., the correspondent epoxide was produced with a yield of 92%.

Example 23

Epoxidation Reaction of Allylbenzene

In a screwed test tube, 1.00 g of fluorapatite (FAp) and 0.079 g (0.021 mmol) of a catalyst (CetylPy)$_3$[PW$_{12}$O$_{40}$] were weighed, and 0.121 g (1.03 mmol) of allylbenzene was added to a solid mixture composed of them, and the mixture was stirred well. Further, 0.11 mL mmol) of 31% aqueous hydrogen peroxide was added and the mixture was stirred well, then, allowed to stand still at 25° C. After 24 hours at 25° C., the correspondent epoxide was produced with a yield of 42% (selectivity 99%).

Example 24

Epoxidation Reaction of Dicyclopentadiene

In a screwed test tube, 1.00 g of fluorapatite (FAp) and 0.079 g (0.021 mmol) of a catalyst (CetylPy)$_3$[PW$_{12}$O$_{40}$] were weighed, and 0.134 g (1.02 mmol) of dicyclopentadiene was added to a solid mixture composed of them, and the mixture was stirred well. Further, 0.33 mL (3.0 mmol) of 31% aqueous hydrogen peroxide was added and the mixture was stirred well, then, allowed to stand still at 25° C. After 96 hours at 25° C., extraction with a solvent was carried out in the same manner as in Example 1, and the solvent was evaporated, to obtain 0.166 g (yield 99%, selectivity 99%) of the correspondent diepoxide.

Example 25

Epoxidation Reaction of 1,5-cyclooctadiene

In a screwed test tube, 1.00 g of diatomaceous earth (Celite545) and 0.077 g (0.020 mmol) of a catalyst (CetylPy)$_3$[PW$_{12}$O$_{40}$] were weighed, and 0.111 g (1.03 mmol) of 1,5-cyclooctadiene was added to a solid mixture composed of them, and the mixture was stirred well. Further, 0.265 mL (2.4 mmol) of 31% aqueous hydrogen peroxide was added and the mixture was stirred well, then, allowed to stand still at 25° C. The correspondent monoepoxide and di epoxide were produced with yields of 45% and 7%, respectively after 5 hours at 25° C., and produced with yields of 19% and 81%, respectively after 17 hours at 25° C.

Example 26

Epoxidation Reaction of (R)-(+)-limonene

In a screwed test tube, 1.00 g of fluorapatite (FAp) and 0.076 g (0.020 mmol) of a catalyst (CetylPy)$_3$[PW$_{12}$O$_{40}$] were weighed, and 0.150 g (1.10 mmol) of (R)-(+)-limonene was added to a solid mixture composed of them, and the mixture was stirred well. Further, 0.22 mL (2.0 mmol) of 31% aqueous hydrogen peroxide was added and the mixture was stirred well, then, allowed to stand still at 25° C. After 14 hours at 25° C., the correspondent monoepoxide was produced with a yield of 61% (selectivity 86%).

Example 27

Oxidation Reaction of Benzylalcohol

In a screwed test tube, 1.00 g of fluorapatite (FAp) and 0.060 g (0.010 mmol) of a catalyst $(CetylPy)_{10}[H_2W_{12}O_{42}]$ were weighed, and 0.108 g (1.00 mmol) of benzylalcohol was added to a solid mixture composed of them, and the mixture was stirred well. Further, 0.11 mL (1.0 mmol) of 31% aqueous hydrogen peroxide was added and the mixture was stirred well, then, allowed to stand still at 25° C. After 24 hours at 25° C., benzaldehyde was produced with a yield of 74%.

Example 28

Oxidation Reaction of α-phenethylalcohol

In a screwed test tube, 1.00 g of fluorapatite (FAp) and 0.059 g (0.010 mmol) of a catalyst $(CetylPy)_{10}[H_2W_{12}O_{42}]$ were weighed, and 0.122 g (1.00 mmol) of α-phenethylalcohol was added to a solid mixture composed of them, and the mixture was stirred well. Further, 0.11 mL (1.0 mmol) of 31% aqueous hydrogen peroxide was added and the mixture was stirred well, then, allowed to stand still at 25° C. After 24 hours at 25° C., the correspondent ketone was produced with a yield of 72%.

Example 29

Oxidation Reaction of p-tolyl methyl sulfide (1)

In a screwed test tube, 1.00 g of fluorapatite (FAp) and 0.039 g (0.010 mmol) of a catalyst $(CetylPy)_3[PW_{12}O_{40}]$ were weighed, and 0.0687 g (0.50 mmol) of p-tolyl methyl sulfide was added to a solid mixture composed of them, and the mixture was stirred well. Further, 0.10 mL (0.90 mmol) of 31% aqueous hydrogen peroxide was added and the mixture was stirred well, then, allowed to stand still at 25° C. After 24 hours at 25° C., the correspondent sulfone was produced with a yield of 87%.

Example 30

Oxidation Reaction of p-tolyl methyl sulfide (2)

In a screwed test tube, 1.00 g of fluorapatite (FAp) and 0.0381 g (0.010 mmol) of a catalyst $(CetylPy)_3[PW_{12}O_{40}]$ were weighed, and 0.138 g (1.00 mmol) of p-tolyl methyl sulfide was added to a solid mixture composed of them, and stirred well. Further, 0.10 mL (0.90 mmol) of 31% aqueous hydrogen peroxide was added and stirred well, then, allowed to stand still at 25° C. After 24 hours at 25° C., the correspondent sulfoxide was produced with a yield of 70%. The sulfone yield was as low as 6%, and the sulfoxide selectivity was 92%.

Example 31

Oxidation Reaction of γ-picoline

In a screwed test tube, 1.00 g of fluorapatite (FAp) and 0.077 g (0.020 mmol) of a catalyst $(CetylPy)_3[PW_{12}O_{40}]$ were weighed, and 0.105 g (1.13 mmol) of γ-picoline was added to a solid mixture composed of them, and stirred well. Further, 0.22 mL (2.00 mmol) of 31% aqueous hydrogen peroxide was added and stirred well, then, allowed to stand still at 50° C. After 5 hours at 50° C., extraction with a solvent was carried out in the same manner as in Example 1, and the solvent was evaporated, to obtain 0.110 g (yield 90%) of the correspondent N-oxide.

The results of the Examples 27-31 show that the oxidation reaction system of the present invention can be applied, not only to an epoxidation reaction, but also to other oxidation reactions of an organic compound, such as oxidation of an alcohol, oxidation of a sulfide, production of an N-oxide from an organic compound having tertiary nitrogen, and the like.

What is claimed:

1. A solid phase reaction system for oxidation of an organic compound having a carbon-carbon double bond, comprising
a mixture of a powdery dispersion medium and a powder of a solid catalyst for the above-described oxidation reaction, the above-described organic compound, and aqueous hydrogen peroxide having a concentration of 5% or more and less than 35%,
wherein the above-described organic compound, the above-described solid catalyst and the above-described aqueous hydrogen peroxide are dispersed in the above-described mixture so that they get into contact mutually;
wherein the solid catalyst is oxides of metals selected from the group consisting of tungsten, molybdenum and vanadium; oxyacids containing metals selected from the group consisting of tungsten, molybdenum and vanadium, and salts thereof; or oxides, halides or sulfates of elements selected from the group consisting of iron, manganese and ruthenium.

2. A solid phase reaction system for oxidation of an organic compound having a carbon-carbon double bond, comprising
a mixture of a powdery dispersion medium and a powder of a solid catalyst for the above-described oxidation reaction, the above-described organic compound, and aqueous hydrogen peroxide having a concentration of 35% or more and 60% or less,
wherein the above-described organic compound, the above-described solid catalyst and the above-described aqueous hydrogen peroxide are dispersed in the above-described mixture so that they get into contact mutually;
wherein the solid catalyst is oxides of metals selected from the group consisting of tungsten, molybdenum and vanadium; oxyacids containing metals selected from the group consisting of tungsten, molybdenum and vanadium, and salts thereof; or oxides, halides or sulfates of elements selected from the group consisting of iron, manganese and ruthenium.

3. The solid phase reaction system for oxidation according to claim 1 or claim 2, wherein the powdery dispersion medium is selected from phosphates, diatomaceous earth, silica, alumina, kaolin, silica alumina and calcium fluoride.

4. A solid phase reaction system for oxidation of an organic compound having a carbon-carbon double bond, comprising
a mixture of a powdery dispersion medium selected from the group consisting of apatite, diatomaceous earth and calcium fluoride and a powder of a solid catalyst for the above-described oxidation reaction, the above-described organic compound and aqueous hydrogen peroxide,
wherein the above-described organic compound, the above-described solid catalyst and the above-described aqueous hydrogen peroxide are dispersed in the above-described mixture so that they get into contact mutually;

wherein the solid catalyst is oxides of metals selected from the group consisting of tungsten, molybdenum and vanadium; oxyacids containing metals selected from the group consisting of tungsten, molybdenum and vanadium, and salts thereof; or oxides, halides or sulfates of elements selected from the group consisting of iron, manganese and ruthenium.

5. The solid phase reaction system for oxidation according to claim 1, 2, or 4, wherein the solid catalyst is selected from the group consisting of the oxides of tungsten or molybdenum, the isopolyacids containing tungsten or molybdenum and the heteropolyacids containing tungsten or molybdenum.

6. The solid phase reaction system for oxidation according to claim 5, wherein the solid catalyst is selected from the group consisting of the isopolyacids and heteropolyacids containing tungsten.

7. The solid phase reaction system for oxidation according to any one of claim 1, 2, or 4, wherein the above-described oxidation is a reaction of inserting oxygen into the carbon-carbon double bond of the above-described organic compound having a carbon-carbon double.

* * * * *